United States Patent [19]
Bavitz

[11] Patent Number: 5,613,852
[45] Date of Patent: Mar. 25, 1997

[54] DENTAL IMPLANT DRILL GUIDE SYSTEM

[75] Inventor: J. Bruce Bavitz, Lincoln, Nebr.

[73] Assignee: Board of Regents Univ of NE at Lincoln, Lincoln, Nebr.

[21] Appl. No.: 369,686

[22] Filed: Jan. 6, 1995

[51] Int. Cl.$^6$ .............................. A61C 8/00; A61C 9/00
[52] U.S. Cl. ............................................ 433/173; 433/214
[58] Field of Search ............................. 433/75, 76, 173, 433/213, 214, 221, 225, 174

[56] References Cited

U.S. PATENT DOCUMENTS

| | | | |
|---|---|---|---|
| 275,491 | 4/1883 | How | 433/221 |
| 400,921 | 4/1889 | Land | 433/225 |
| 3,407,503 | 10/1968 | Pompa | 433/76 |
| 4,708,654 | 11/1987 | Branemark | 433/213 |
| 4,752,225 | 6/1988 | Bori | 433/221 |
| 4,778,388 | 10/1988 | Yuda et al. | 433/221 |
| 4,871,313 | 10/1989 | Maillefer | 433/225 |
| 4,975,059 | 12/1990 | Sendax | 433/173 |
| 5,007,833 | 4/1991 | Barbone | 433/173 X |
| 5,015,183 | 5/1991 | Fenick | 433/76 |
| 5,133,660 | 7/1992 | Fenick | 433/76 |
| 5,350,297 | 9/1994 | Cohen | 433/76 |

OTHER PUBLICATIONS

*Journal of Esthetic Dentistry*, 1993 vol. 5/No. 6, "Effect of Implant Restoration Design", Richard J. Lazzara, DMD, MScD.

Primary Examiner—Nicholas D. Lucchesi
Attorney, Agent, or Firm—Zarley, McKee, Thomte, Voorhees & Sease; Mark D. Frederiksen

[57] ABSTRACT

A method for imbedding a dental implant includes the initial step of casting a model of the patient's jaw and teeth in the vicinity of the implant site. A pilot hole is drilled in the implant site of the model, correlating to the ideal angle and location of the implant in the patient's jaw. A guide rod is provided for forming a guide hole in a stent, with a generally cylindrical shaft and a screw portion mounted at the lower end of the shaft. The screw portion is threaded into the pilot hole with the upper portion of the guide rod projecting coaxially in the desired location of the implant. A stent is then fabricated on the model, with the upper end of the guide rod accessible to a removal tool. A crossed slot in the upper end of the guide rod permits use of a screwdriver to remove the guide rod from the stent and model, thereby forming a guide hole in the stent. The guide sleeve is then journaled in the guide hole in the stent, and the stent is placed onto the patient's jaw and teeth. A drill bit is journaled through the guide sleeve to form a guide bore in the patient's jaw, and then the stent is removed from the patient's jaw. Finally, a dental implant is embedded in the guide bore.

3 Claims, 2 Drawing Sheets

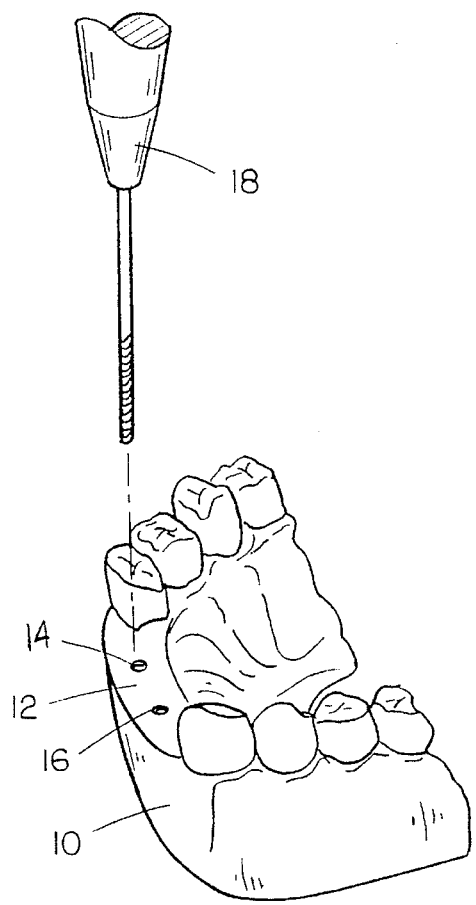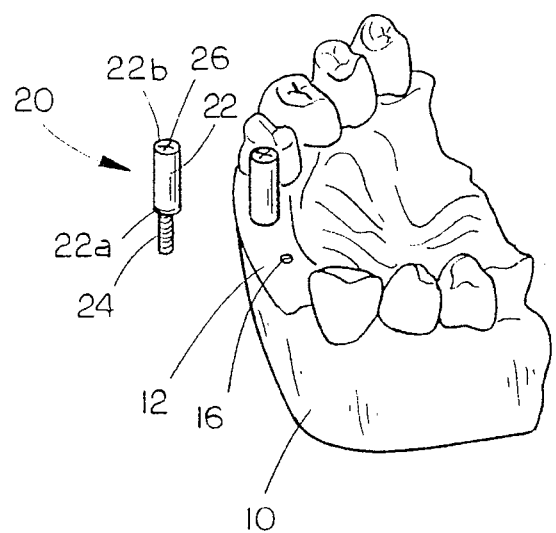
FIG. 1
FIG. 2
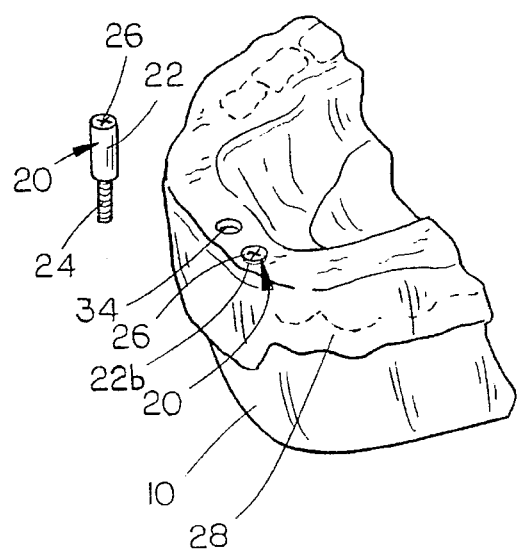
FIG. 3

DENTAL IMPLANT DRILL GUIDE SYSTEM

TECHNICAL FIELD

The present invention relates generally to a drill guide system for dental implants, and more particularly to an improved pilot rod for guiding a drill utilized in dental implants, and a method for guiding the drill in the implant process.

BACKGROUND OF THE INVENTION

The use of tooth implants is gaining popularity to replace lost teeth. However, the dental implant process relies on precise placement of the implants in the upper and lower jaw bones for an esthetic and functional result. Location of the hole for the implant, and orientation of that hole, are critical to the success of the implantation process. Of equal importance is the drilling of a concentric hole, the diameter of which is equal to the implant. The body will reject implants placed in eccentric, imprecisely prepared sites.

SUMMARY OF THE INVENTION

It is therefore a general object of the present invention to provide a guide system for the dental implant drill to provide a precisely angled and located guide hole for a dental implant.

Another object is to provide a guide pin which is easily removable from a dental cast to provide an optimally located guide bore for a drill.

Still another object of the present invention is to provide a method for drilling a bore for a dental implant using a guide hole formed in a dental stent.

An additional object of the present invention is to utilize removable drill sleeves to drill a concentric hole in a patient's jaws the same diameter as the intended dental implant.

These and other objects will be apparent to those skilled in the art.

The method for imbedding a dental implant of the present invention includes the initial step of casting a model of the patient's jaw and teeth in the vicinity of the implant site. A pilot hole is drilled in the implant site of the model, correlating to the ideal angle and location of the implant in the patient's jaw. A guide rod is provided for forming a guide hole in a stent, with a generally cylindrical shaft and a screw portion mounted at the lower end of the shaft. The screw portion is threaded into the pilot hole with the upper portion of the guide rod projecting coaxially in the desired location of the implant. A stent is then fabricated on the model, with the upper end of the guide rod accessible to a removal tool. A crossed slot in the upper end of the guide rod permits use of a screwdriver to remove the guide rod from the stent and model, thereby forming a guide hole in the stent. The guide sleeve is then journaled in the guide hole in the stent, and the stent is placed onto the patient's jaw and teeth. A drill bit is journaled through the guide sleeve to form a guide bore in the patient's jaw, and then the stent is removed from the patient's jaw. Finally, a dental implant is embedded in the guide bore.

BRIEF DESCRIPTION OF THE DRAWINGS

FIG. 1 is a perspective view of a model made from an impression of a patient's teeth illustrating the implant void, and showing a drill forming guide holes in the model;

FIG. 2 is a perspective view of the model of FIG. 1 with one guide rod inserted in one pilot hole and a second guide rod removed from the second pilot hole;

FIG. 3 is a perspective view of a splint or stent formed on the model of a patient's teeth, with one guide rod removed therefrom;

DESCRIPTION OF THE PREFERRED EMBODIMENT

Figure 4:
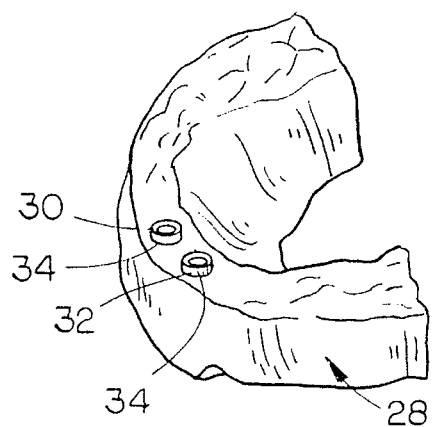
FIG. 4 is a perspective view of the stent with two different drill sleeves inserted within the guide openings formed by the guide rods.

Referring now to the drawings, in which similar or corresponding parts are identified with the same reference numeral, and more particularly to FIG. 1, an impression is taken of a patient's teeth in the vicinity of the area in which the implant is to be placed. From the impression taken, a model 10 is cast of the patient's teeth with a void 12 where the dental implants will be inserted. For purposes of illustration, the two lower incisors of a patient's mouth are the intended location of dental implants.

Pilot holes 14 and 16 are then formed in model 10 using a drill 18. Typically, model 10 is attached to a surveying table such that a drill press may be utilized to drill pilot holes 14 and 16 in the implant void 12, at the optimal location and angle.

Referring now to FIG. 2, after pilot holes 14 and 16 have been drilled into void 12, a guide rod 20 is threaded into each pilot hole. Each guide rod 20 includes a cylindrical shaft 22 having upper and lower ends, and a threaded screw 24 mounted coaxially with shaft 22 at the lower end thereof. Screw 24 has a diameter less than the diameter of shaft 22 such that the lower end 22a of shaft 22 forms a shoulder which will contact the surface of implant void 12 when screw 24 is threaded into a pilot hole 16. Preferably, screw 24 is tapered with deep threads which will tap into model 10 while guide rod 20 is inserted in pilot hole 16. The diameter of screw 24 is slightly larger than drill 18.

A crossed slot 26 is formed in the upper end 22b of shaft 22, to receive a corresponding screwdriver. In this way, each guide rod 20 may be threaded into the associated pilot hole 16 using a screwdriver.

Once guide rods 20 have been inserted in the pilot holes 16, a standard dental acrylic is used to fabricate stent 28 which extends over the implant void 12, as shown in FIG. 3, with the upper ends 22b of guide rod shafts 22 projecting slightly upwardly therefrom. After stent 28 has cured, guide rods 20 may be removed by engaging a screwdriver in the crossed slot 26 of each guide rod, and rotating them counterclockwise to unthread the screw 24 from the model 10.

Once guide rods 20 have been removed from stent 28, guide sleeve 30 and 32 are inserted within the guide bores 34 left by the guide rods 20, as shown in FIG. 4. In order to provide a close fit of guide sleeves 30 or 32 within stent 28, shaft 22 of guide rods 20 have the same external diameter as guide sleeves 30 and 32.

Figure 5:
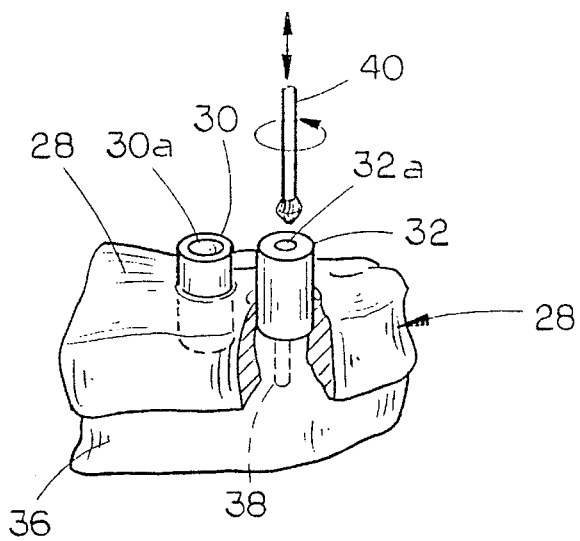
FIG. 5 is a fragmentary view of the stent of FIG. 4 placed onto the teeth in a patient's mouth to illustrate the drilling of a pilot bore for the implant.
Figure 6:
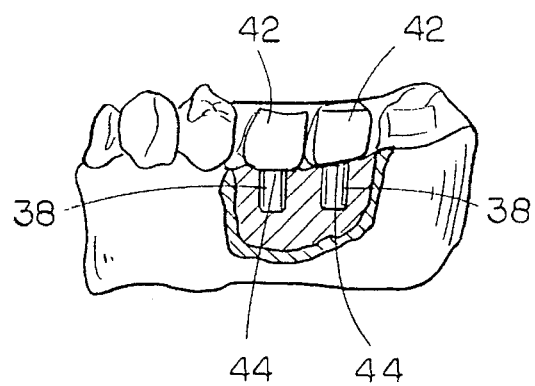
FIG. 6 is a fragmentary view of the patient's teeth with the implant in place.

Referring now to FIG. 5, the stent 28 is fitted to the patient's lower jaw with guide sleeves 30 and 32 located precisely over the implant area with the guide sleeves properly angled for drilling an implant bore directly into the patient's jaw 36. The size of the internal bore 30a and 32a of guide sleeves 30 and 32, respectively, is dictated by the diameter of the dental implant to be utilized, an average 4.0 mm. The arrangement is such that the center of the respective guide sleeve 30 and 32 is disposed in substantial alignment with the trajectory of a proposed implant bore 38, shown in hidden lines in FIG. 5. Implant bore 38 is drilled utilizing a conventional dental drill 40 journaled through guide bore 30a or 32a into the patient's jaw 36. It is common practice to prepare the implant recipient site 38 in stages, beginning with narrow diameter drills 40 and working up to the precise diameter of the final implant 44. The guide sleeves 30 and 32 are changed, correspondingly, to match the ascending diameter of the varying drill bits 40.

After the implant bore 38 has been drilled, stent 28 is removed from the patient's jaw 36 and the dental implants 44 are placed in the precisely prepared sites 38. The prosthetic teeth 42 are subsequently formed in the appropriate shape dictated by esthetics and function.

Whereas the invention has been shown and described in connection with the preferred embodiment thereof, many modifications, substitutions and additions may be made which are within the intended broad scope of the appended claims.

I claim:

1. A method of imbedding a dental implant, comprising the steps of:

casting a model of a patient's jaw and teeth in the vicinity of an implant site;

drilling a pilot hole in the model in an implant site, correlating to the ideal angle and location desired of the implant in the patient's jaw;

journaling a lower portion of a guide rod into the pilot hole with an upper portion of the guide rod projecting coaxially in the desired location of the implant, the guide rod having a slot in an upper end thereof for receipt of a removal tool;

fabricating a stent on the model, with the upper end of the guide rod accessible to a removal tool;

removing the guide rod from the stent and model, to form a guide hole in the stent;

journaling a guide sleeve in the guide hole in the stent;

placing the stent onto the patient's jaw and teeth;

utilizing said guide sleeve to guide a drill bit in forming a guide bore in the patient's jaw;

removing the stent from the patient's jaw; and imbedding a dental implant in the guide bore.

2. The method of claim 1, wherein the step of journaling the lower portion of the guide rod into the pilot hole includes the steps of:

providing said guide rod with an upper cylindrical shaft and a lower threaded screw; and threading the screw into the pilot hole.

3. The method of claim 2, wherein the step of removing the guide rod includes engaging a removal tool with the upper end of the guide rod shaft to rotate the guide rod and unscrew the screw from the pilot hole.

* * * * *